(12) United States Patent
Dagsland et al.

(10) Patent No.: US 7,143,764 B1
(45) Date of Patent: Dec. 5, 2006

(54) INHALATION DEVICE

(75) Inventors: Allan Dagsland, Karlshamn (SE); Risto Virtanen, Nurmijärvi (FI)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/068,374

(22) Filed: May 8, 1998

Related U.S. Application Data

(63) Continuation of application No. PCT/SE98/00459, filed on Mar. 13, 1998.

(51) Int. Cl.
*A61M 15/00* (2006.01)

(52) U.S. Cl. .......................... 128/203.15; 128/203.12; 128/203.21; 128/205.23

(58) Field of Classification Search ........... 128/203.12, 128/203.15, 202.22, 205.23, 203.21; 222/636; 607/58

See application file for complete search history.

(56) References Cited

U.S. PATENT DOCUMENTS

| | | | | | |
|---|---|---|---|---|---|
| 4,668,218 | A | * | 5/1987 | Virtanen | 604/58 |
| 4,817,822 | A | * | 4/1989 | Rand et al. | 222/38 |
| 5,174,473 | A | * | 12/1992 | Marelli | 222/38 |
| 5,482,030 | A | * | 1/1996 | Klein | 128/200.23 |
| 5,687,710 | A | * | 11/1997 | Ambrosio et al. | 128/203.15 |
| 5,699,789 | A | * | 12/1997 | Hendricks | 128/203.15 |
| 5,740,792 | A | * | 4/1998 | Ashley et al. | 128/203.15 |
| 5,829,434 | A | * | 11/1998 | Ambrosio et al. | 128/203.15 |
| 6,240,918 | B1 | * | 6/2001 | Ambrosio et al. | 128/205.15 |

FOREIGN PATENT DOCUMENTS

| | | |
|---|---|---|
| EP | 0 237 507 A1 | 9/1987 |
| WO | WO 86/05991 | 10/1986 |
| WO | WO 92/00771 | 1/1992 |

OTHER PUBLICATIONS

Copy of PCT Search Report PCT/SE98/00459.

* cited by examiner

*Primary Examiner*—Aaron J. Lewis
(74) *Attorney, Agent, or Firm*—Fish & Richardson P.C.

(57) ABSTRACT

A powder inhaler for administering powder by inhalation which includes: an inhaler body having an opening therein; an inhalation unit disposed in the inhaler body, the inhalation unit including an inhalation channel through which powder is in use inhaled; a dosing unit for providing a dose of powder to the inhalation channel disposed in the inhaler body so as to be rotatable about the central axis thereof, wherein the dosing unit includes a central shaft which is co-axial with the central axis of the inhaler body and has a spiral groove or protrusion on the end face thereof; and an indicating wheel for providing an indication as to the usage of the inhaler disposed in the inhaler body, the indicating wheel having a toothed periphery for engaging the spiral groove or protrusion on the shaft and being disposed such that at least a part thereof is visible through the opening and so as to be rotatable within a diametrical plane containing the central axis of the inhaler body. One side surface of the indicating wheel includes at least one indication which is representative of the usage of the inhaler. In addition, the inhaler body includes a recess in which the opening is provided. The opening allows at least a part of the one side surface of the indicating wheel to be viewed.

13 Claims, 7 Drawing Sheets

INHALATION DEVICE

This is a continuation of International Patent Application No. PCT/SE98/00459, with an international filing date of 13 Mar. 1998, now pending.

BACKGROUND

The present invention relates to a powder inhaler for administering powder by inhalation.

A number of powder inhalers are known which use different systems for introducing a dose of powder into an air stream. Typically, the powder is inhaled into the lungs of a patient in order to treat, for example, asthma.

One such powder inhaler is disclosed in WO-A-86/05991. This inhaler includes a flow path, which comprises an inhalation channel and a mouthpiece comprising an air chamber and an outlet nozzle, through which a stream of air is drawn during inhalation by a user, and means for introducing powder into the inhalation channel. During inhalation, air is first drawn into and through the inhalation channel so as to pick up powder. The stream of air containing powder is then drawn through the air chamber and out of the outlet nozzle of the mouthpiece.

FIG. 1 illustrates such a powder inhaler. The inhaler comprises a mouthpiece 2 comprising an air chamber (not illustrated) and an outlet nozzle 4, an inhaler body 6 and a rotatable grip portion 8 for operating a dosing mechanism for providing doses of powder for inhalation. The inhaler body 6 includes an opening 10 which is filled with a window 12 through which an indicating wheel 42 is visible so as to provide an indication as to the usage of the inhaler.

FIG. 2 illustrates in exploded view component parts disposed within and to the inhaler body 6. The inhaler body 6 is capped with a divider 14 which is fixed thereto and separates the air chamber in the mouthpiece 2 from a major part of the inhaler body 6. For aesthetic reasons the inhaler body 6 is an opaque moulding. The divider 14 is a transparent moulding which has a depending tongue 15, a part of which forms the window 12. When the inhaler is assembled, the only part of the divider 14 which is visible is the part of the tongue 15 forming the window 12, and thus the overall appearance of the inhaler is unaffected.

Within the inhaler body 6 are housed the component parts of the dosing mechanism. These component parts include a dosing unit 16 which comprises a plurality of dosing means 18 and a central axial shaft 20, an inhalation unit 22 which comprises an inhalation channel 24 and a storage unit 26 which comprises a storage chamber 28 for storing powder. The above-mentioned component parts of the dosing mechanism are assembled by passing the inhalation channel 24 through an opening 30 in the storage unit 26 and passing the shaft 20 through central openings 32, 34 in the inhalation unit 22 and the storage unit 26 respectively. When so assembled, the upper ends of the inhalation channel 24 and the storage chamber 28 pass respectively through first and second openings 36, 38 in the divider 14.

In use, powder is transferred from the storage chamber 28 to one of the dosing means 18 and, with rotation of the dosing unit 16, the one dosing means 18 provides a dose of powder to the inhalation channel 24. On inhalation by a user the powder is drawn up through the air chamber and out of the outlet nozzle 4 of the mouthpiece 2.

As illustrated in FIGS. 2 and 3, the divider 14 further comprises supporting means 40 for rotatably supporting an indicating wheel 42. The indicating wheel 42 has a plurality of teeth 44 disposed around the periphery thereof which engage with a spiral groove or protrusion 46 on the end face of the shaft 20 of the dosing unit 16. The supporting means 40 is configured to align the indicating wheel 42 such that a part of the periphery thereof is disposed adjacent the inner surface of the window 12.

In use, as the dosing unit 16 is rotated, the spiral groove or protrusion 46 engages with one or more of the teeth 44 on the indicating wheel 42 so as to rotate the same. In this way, by providing a coloured marking on the periphery of the indicating wheel 42, it is possible to provide the user with a visible indication at the window 12 as to the usage of the inhaler. Whilst the above-described known powder inhaler functions quite adequately, it is an aim of the present invention to provide a powder inhaler which more visibly indicates the usage of the inhaler. It is a further aim of the present invention to provide a powder inhaler having fewer components and hence reduced manufacturing complexity.

SUMMARY OF THE INVENTION

In one aspect the present invention provides a powder inhaler, comprising: an inhaler body having an opening therein; an inhalation unit disposed in the inhaler body, the inhalation unit comprising an inhalation channel through which powder is in use inhaled; a dosing unit for providing a dose of powder to the inhalation channel disposed in the inhaler body so as to be rotatable about the central axis thereof, wherein the dosing unit comprises a central shaft which is co-axial with the central axis of the inhaler body and has a spiral groove or protrusion on the end face thereof; and an indicating wheel for providing an indication as to the usage of the inhaler disposed in the inhaler body, the indicating wheel having a toothed periphery for engaging the spiral groove or protrusion on the shaft and being disposed such that at least a part thereof is visible through the opening and so as to be rotatable within a diametrical plane containing the central axis of the inhaler body; characterized in that one side surface of the indicating wheel includes at least one indication which is representative of the usage of the inhaler and in that the inhaler body includes a recess in which the opening is provided, the opening allowing at least a part of the one side surface of the indicating wheel to be viewed.

Embodiments of this aspect of the invention may include one or more of the following features.

Preferably the inhaler further comprises a storage unit disposed in the inhaler body, the storage unit comprising a storage chamber for storing powder.

More preferably, the storage unit is formed of a transparent material and the inhaler further comprises a portion which substantially fills the opening.

Preferably, the inhalation unit and the storage unit are formed as a single integral unit.

Preferably, the inhaler further comprises a divider substantially closing one end of the inhaler body.

More preferably, the recess comprises first and second opposing surfaces which are substantially parallel to the major surface of the divider and at least first and second side surfaces joining the first and second opposing surfaces, the opening being formed in one of the side surfaces.

Preferably, the inhaler body and the divider are formed as a single integral unit.

In one embodiment the storage unit further comprises supporting means for rotatably supporting the indicating wheel.

In another embodiment the divider comprises supporting means for rotatably supporting the indicating wheel.

Preferably, the inhaler body further comprises an air inlet in a side wall thereof, the air inlet allowing air to be drawn to the dosing unit and through the inhalation channel.

More preferably, the air inlet is provided in the recess.

Preferably, the inhaler body is substantially cylindrical.

Preferably, the one side surface of the indicating wheel includes numerals indicating the number of doses administered and/or remaining.

Preferably, the one side surface of the indicating wheel includes an at least part circular band of varying width indicating the number of doses administered and/or remaining.

In another aspect the invention provides a method of constructing an inhaler for administering powder by inhalation, comprising the steps of: providing an inhaler body having an opening therein; fitting an inhalation unit comprising an inhalation channel through which powder is in use inhaled in the inhaler body; fitting a dosing unit for providing a dose of powder to the inhalation channel in the inhaler body so as to be rotatable about the central axis thereof, wherein the dosing unit comprises a central shaft which is co-axial with the central axis of the inhaler body and has a spiral groove or protrusion on the end face thereof; and fitting an indicating wheel having a toothed periphery in the inhaler body in such a manner that the toothed periphery engages the spiral groove or protrusion on the shaft and so as to be rotatable in a diametrical plane containing the central axis of the inhaler body, wherein at least a part of the indicating wheel is visible through the opening so as to provide an indication as to the usage of the inhaler; characterized in that the method further comprises the steps of providing one side surface of the indicating wheel with at least one indication which is representative of the usage of the inhaler and providing the inhaler body with a recess in which the opening is provided, the opening allowing at least a part of the one side surface of the indicating wheel to be viewed.

Preferably, the step of providing an inhaler body comprises the step of providing as a single integral unit an inhaler body with a divider substantially closing one end thereof.

Medicaments suitable for administration by the powder inhaler of the present invention are any which may be delivered by inhalation and include for example β2-adrenoreceptor agonists, for example, salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators, for example, ipratropium bromide and the like; glucocorticosteroids, for example, beclomethasone, fluticasone, budesonide, tipredane, dexamethasone, betamethasone, fluocinolone, triamcinolone acetonide, mometasone and the like, and their pharmacologically acceptable esters and salts; antiallergic medicaments, for example, sodium cromoglycate and nedocromil sodium; expectorants; mucolytics; antihistamines; cyclooxygenase inhibitors; leukotriene synthesis inhibitors; leukotriene antagonists; phospholipase-A2 (PLA2) inhibitors; platelet aggregating factor (PAF) antagonists and prophylactics of asthma; antiarrhythmic medicaments; tranquilisers; cardiac glycosides; hormones; antihypertensive medicaments; antidiabetic medicaments; antiparasitic medicaments; anticancer medicaments; sedatives; analgesic medicaments; antibiotics; antirheumatic medicaments; immunotherapies; antifungal medicaments; antihypotension medicaments; vaccines; antiviral medicaments; proteins; polypeptides and peptides, for example, peptide hormones and growth factors; polypeptide vaccines; enzymes; endorphines; lipoproteins and polypeptides involved in the blood coagulation cascade; vitamins; and others, for example, cell surface receptor blockers, antioxidants, free radical scavengers and organic salts of N,N'-diacetylcystine.

Preferred embodiments of the present invention will now be described hereinbelow by way of example only with reference to the accompany drawings.

DETAILED DESCRIPTION OF THE PREFERRED EMBODIMENTS

Structurally, the powder inhalers in accordance with the preferred embodiments of the present invention have many features in common with the above-described known powder inhaler. For this reason, and in order to avoid unnecessary duplication of description, only the structural differences will be described in detail and reference is made to the preceding description of the known powder inhaler.

Figures 1, 2:
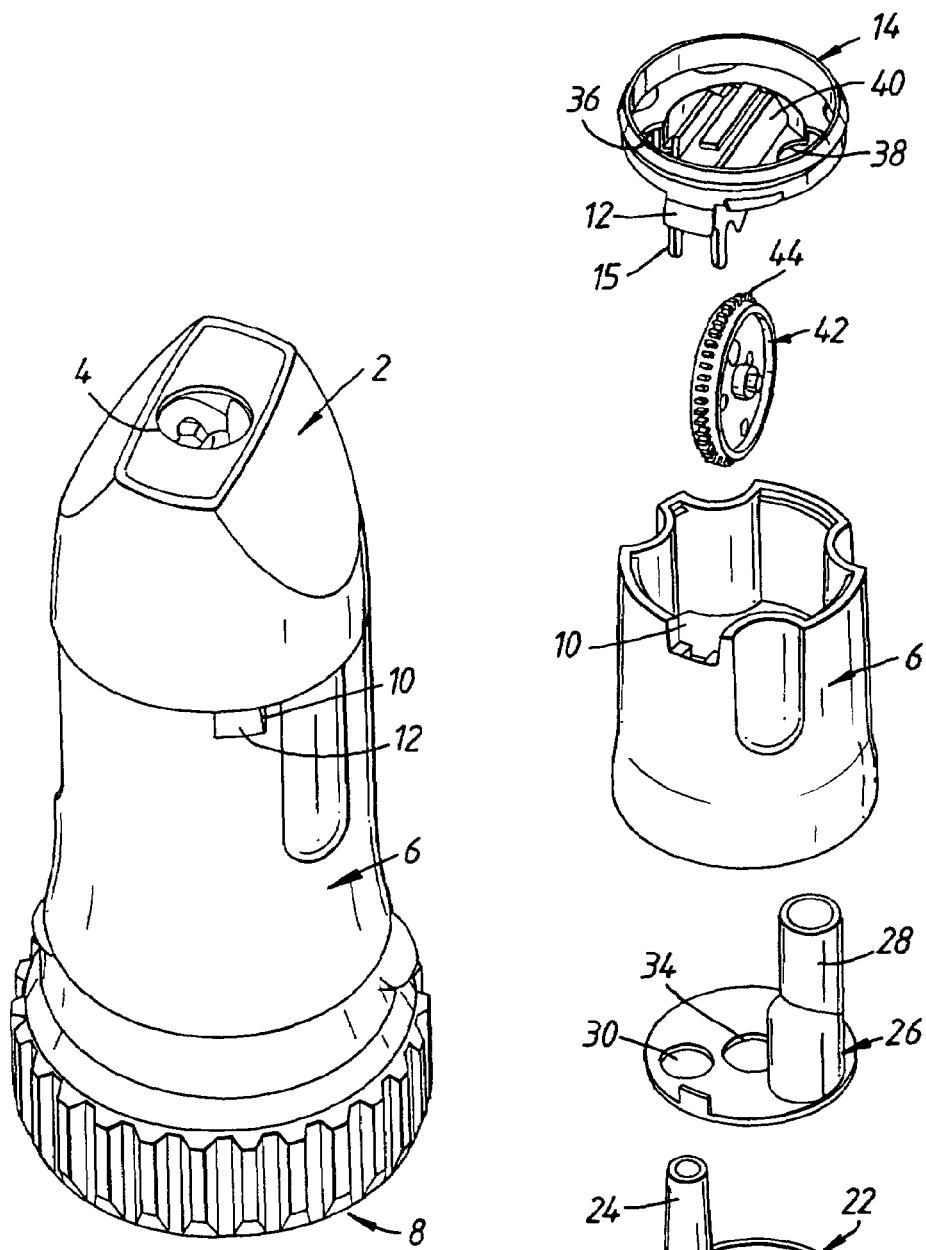
FIG. 1 illustrates a perspective view of a known powder inhaler.
FIG. 2 illustrates in exploded view component parts of the inhaler of FIG. 1.
Figure 3:
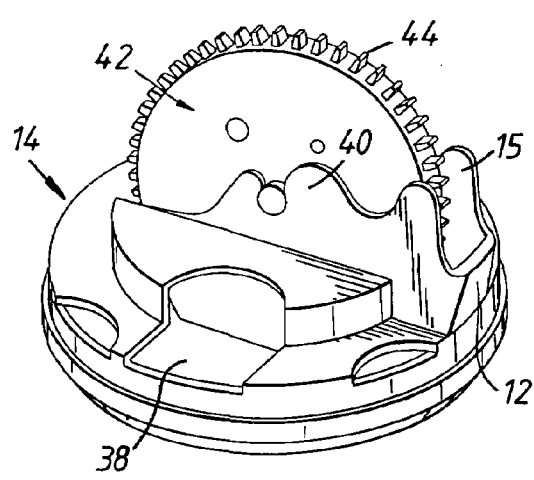
FIG. 3 illustrates component parts of the inhaler of FIG. 1.
Figure 4:
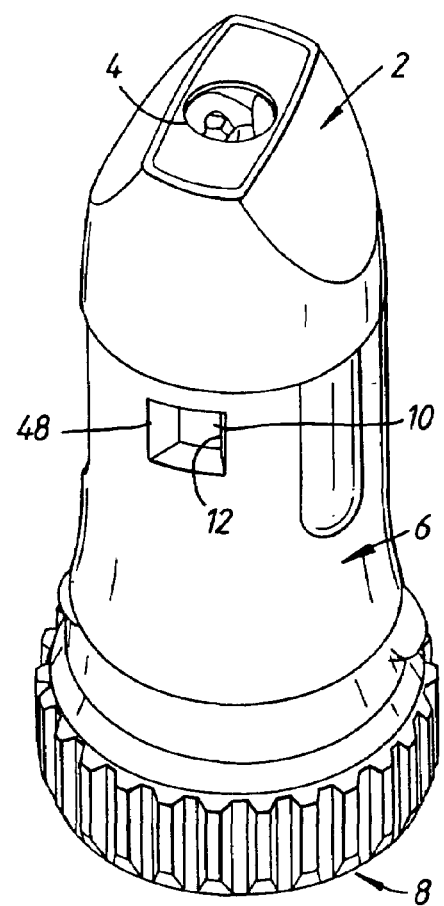
FIG. 4 illustrates a perspective view of a powder inhaler in accordance with a first embodiment of the present invention.

FIG. 4 illustrates a powder inhaler in accordance with a first embodiment of the present invention.

This inhaler is a modification of the above-described known powder inhaler. This inhaler differs from the above-described known powder inhaler in that the inhaler body 6 includes a recess 48 in a side surface of which is provided the opening 10, which recess 48 is located such that the opening 10 is adjacent one of the side surfaces of the indicating wheel 42, and in that the side surface of the indicating wheel 42 adjacent the opening 10 includes an indication or indications representative of the usage of the inhaler. As in the above-described known powder inhaler, the indicating wheel 42 is rotatably supported to the underside of the divider 14. In a preferred embodiment one or both of the inhalation unit 22 and the storage unit 26 are formed together with the inhaler body 6 as a single integral unit.

Figure 5:
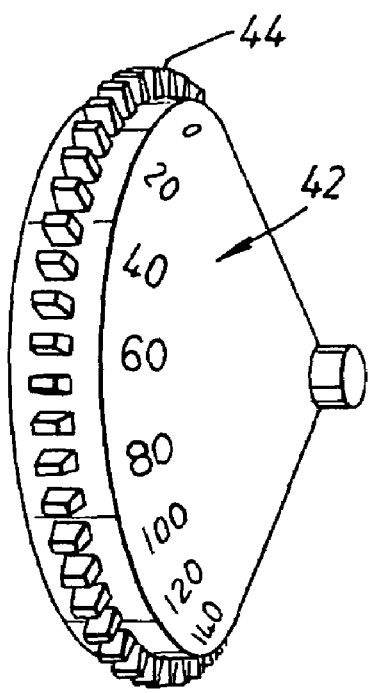
FIGS. 5 and 6 illustrate indicating wheels for use with the powder inhaler of FIG. 4.
Figure 6:
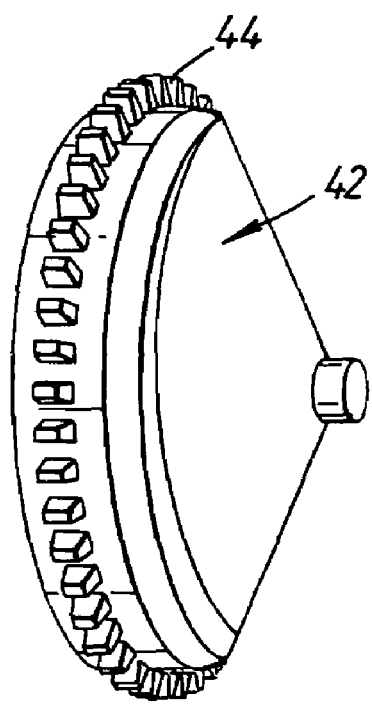

In one embodiment the indicating wheel 42 can be provided with numeric indications of increasing or decreasing value, for indicating the number of times the inhaler has been operated or the number of times the inhaler may still be operated. In another embodiment the indicating wheel 42 may alternatively, or additionally, be provided with a circumferential band of changing width along its length, such that the width visible through the window 12 is representative of the number of doses delivered. Colour changes may also be used to indicate the number of doses delivered or remaining. Such colour changes may be applied in conjunction with the indications described hereinabove. For instance, by using numerals of different colour, or by using a band, the colour of which changes along its length. In a preferred embodiment, in order to assist viewing, the side surface of the indicating wheel 42 adjacent the window 12 can be formed as a conical surface, with the surface of the cone enclosing an angle of from 10° to 30°, preferably about 15°, with the rotational plane of the indicating wheel 42. FIGS. 5 and 6 illustrate preferred indicating wheels 42.

In this embodiment the recess 48 is configured such that the side surface thereof in which the opening 10 is provided is parallel to the adjacent side surface of the indicating wheel 42. It will be appreciated, however, that, for the purposes of viewing the indicating wheel 42, it is sufficient that the opening 10 has a radial component. It will also be appreciated that the recess 48 can have any shape which allows a user to view the adjacent side surface of the indicating wheel 42 through the opening 10.

Figure 7:
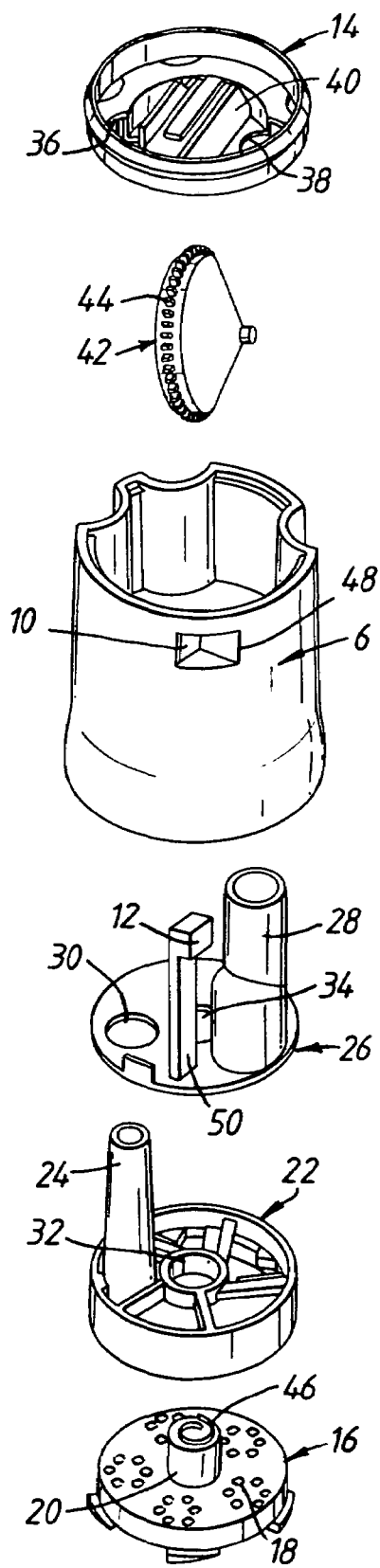
FIG. 7 illustrates in exploded view component parts of a powder inhaler in accordance with a second embodiment of the present invention.

FIG. 7 illustrates in exploded view component parts disposed within and to the inhaler body 6 of a powder inhaler in accordance with a second embodiment of the present invention.

This inhaler is a modification of the inhaler of the above-described first embodiment. This inhaler differs from the inhaler of the above-described first embodiment in that the recess 48 in the inhaler body 6 is of different shape. In this embodiment the recess 48 is of triangular cross-section. It will be noted, however, that in common with the inhaler of the above-described first embodiment the opening 10 in the recess 48 has a radial component. This inhaler further differs from the inhaler of the above-described first embodiment in that the divider 14 does not include a depending tongue 15, but rather the storage unit 26 is formed from a transparent material and comprises an upstanding tongue 50, one part, in this embodiment the distal end, of which is shaped and dimensioned so as to provide the window 12 and fill the opening 10 when the storage unit 26 is fitted in the inhaler body 6.

Figure 8:
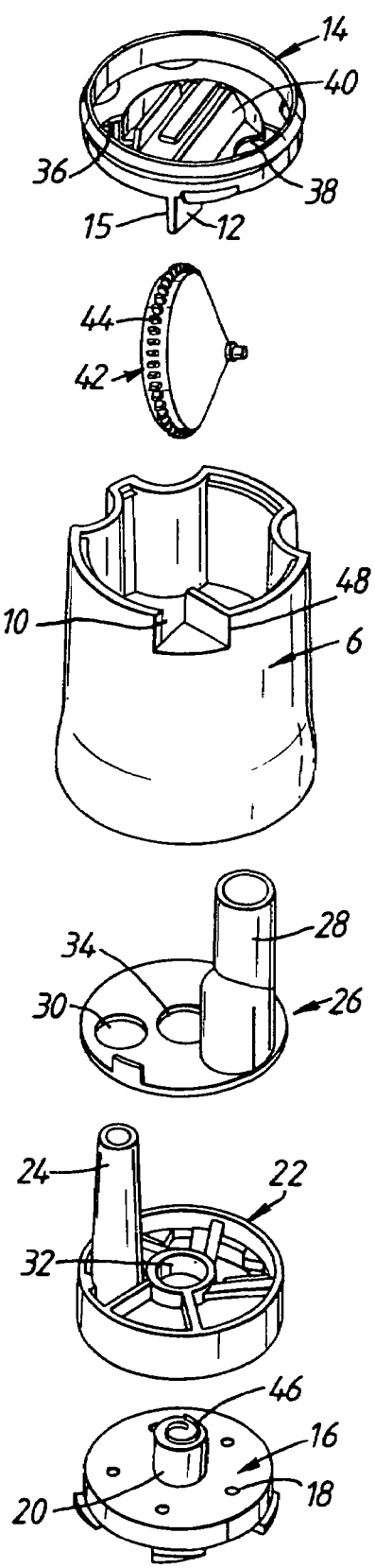
FIG. 8 illustrates in exploded view component parts of a powder inhaler in accordance with a third embodiment of the present invention.

FIG. 8 illustrates in exploded view component parts disposed within and to the inhaler body 6 of a powder inhaler in accordance with a third embodiment of the present invention.

This inhaler is a modification of the inhaler of the above-described first embodiment. This inhaler differs from the inhaler of the above-described first embodiment in that the recess 48 in the inhaler body 6 is of different shape. In this embodiment the recess 48 is, similarly to the recess 48 of the above-described second embodiment, of triangular cross-section. It will be noted, however, that again in common with the inhaler body 6 of the above-described first embodiment the opening 10 in the recess 48 has a radial component. This inhaler further differs from the above-described first embodiment in that the tongue 15 depending from the divider 14 is oriented substantially radially as opposed to circularly so as to align with the opening 10 in the recess 48. Again, as in the above-described known powder inhaler, the indicating wheel 42 is rotatably supported to the underside of the divider 14.

Figure 9:
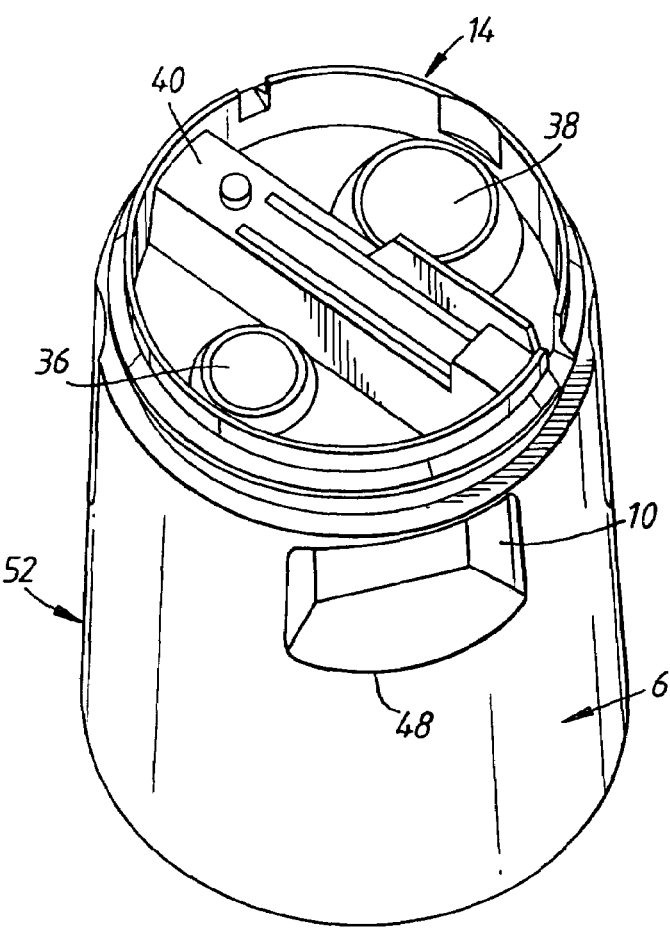
FIGS. 9 and 10 illustrate component parts of a powder inhaler in accordance with a fourth embodiment of the present invention.
Figure 10:
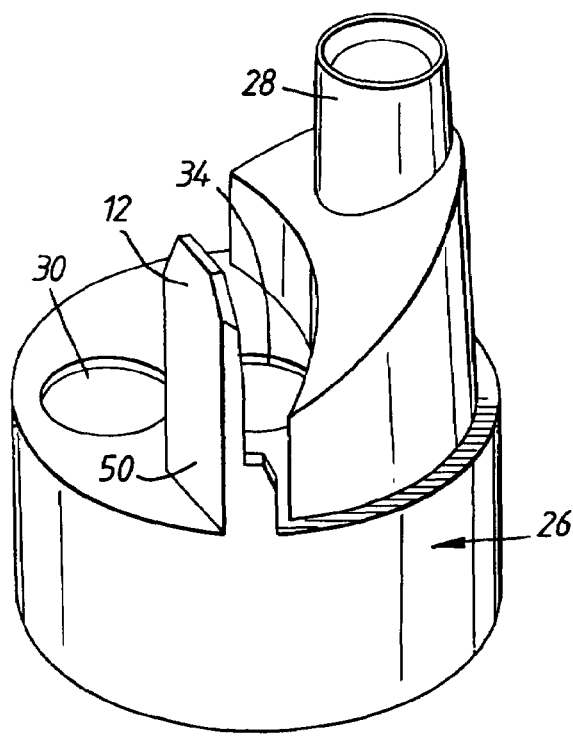

FIGS. 9 and 10 illustrate respectively a body part 52 and a storage unit 26 of a powder inhaler in accordance with a fourth embodiment of the present invention.

This inhaler is a modification of the inhaler of the above-described first embodiment. This inhaler differs from the inhaler of the above-described first embodiment in comprising a body part 52 which is a single part moulded from an opaque material that comprises both the inhaler body 6 and the divider 14. This inhaler further differs from the inhaler of the above-described first embodiment in that the divider 14 does not include a depending tongue 15, but rather the storage unit 26 is formed from a transparent material and comprises an upstanding tongue 50, one part, in this embodiment the distal end, of which is shaped and dimensioned so as to provide the window 12 and fill the opening 10 when the storage unit 26 is fitted in the inhaler body 6. As in the above-described known powder inhaler, the indicating wheel 42 is rotatably supported to the underside of the divider 14.

Figure 11:
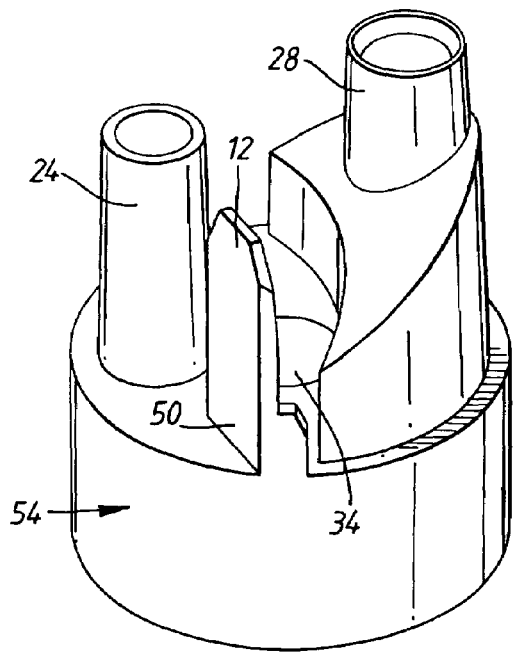
FIG. 11 illustrates a component part of a powder inhaler in accordance with a fifth embodiment of the present invention.

FIG. 11 illustrates a structural unit 54 of a powder inhaler in accordance with a fifth embodiment of the present invention.

This inhaler is a modification of the inhaler of the above-described fourth embodiment. This inhaler differs from the inhaler of the above-described fourth embodiment in comprising a structural unit 54 which is a single part moulded from a transparent material and combines both the inhalation unit 22 and the storage unit 26.

Figure 12:
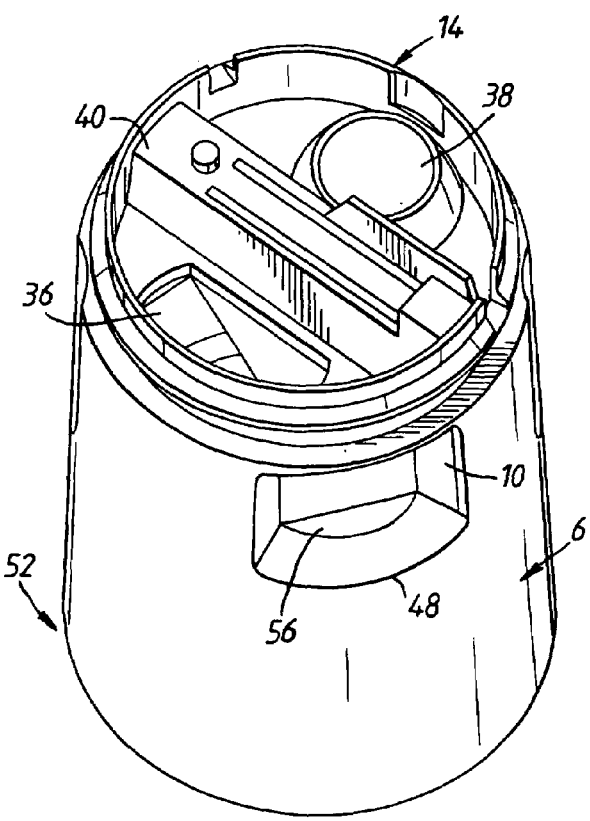
FIGS. 12 and 13 illustrate component parts of a powder inhaler in accordance with a sixth embodiment of the present invention.
Figure 13:
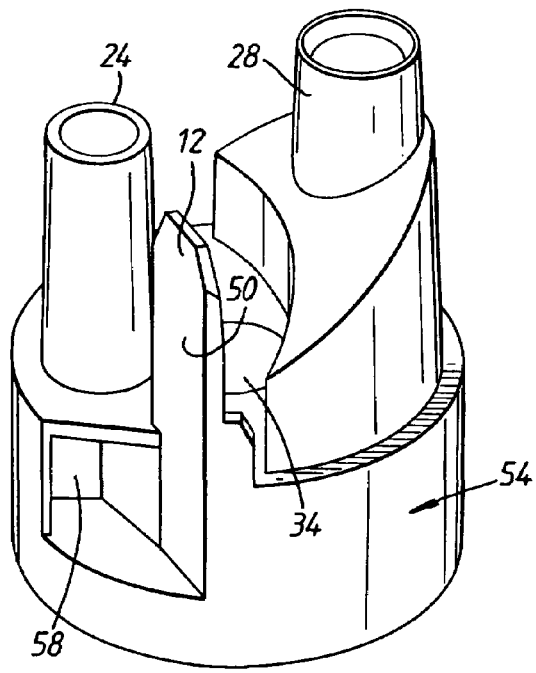

FIGS. 12 and 13 illustrate respectively a body part 52 and a structural unit 54 of a powder inhaler in accordance with a sixth embodiment of the present invention.

This inhaler is a modification of the inhaler of the above-described fifth embodiment. In this embodiment the body part 52 differs in that a lower section of the recess 48 in the inhaler body 6 is cut away to provide an opening 56 into the inhaler body 6 and in that the lower end of the inhalation channel 24 is provided with a lateral opening 58. During inhalation by a user, air is drawn through the opening 56 in the recess 48 and then the opening 58 in the inhalation channel 24 where a dose of powder is entrained, which powder is then drawn up the inhalation channel 24 into and through the air chamber and out of the outlet nozzle 4 of the mouthpiece 2.

Figure 14:
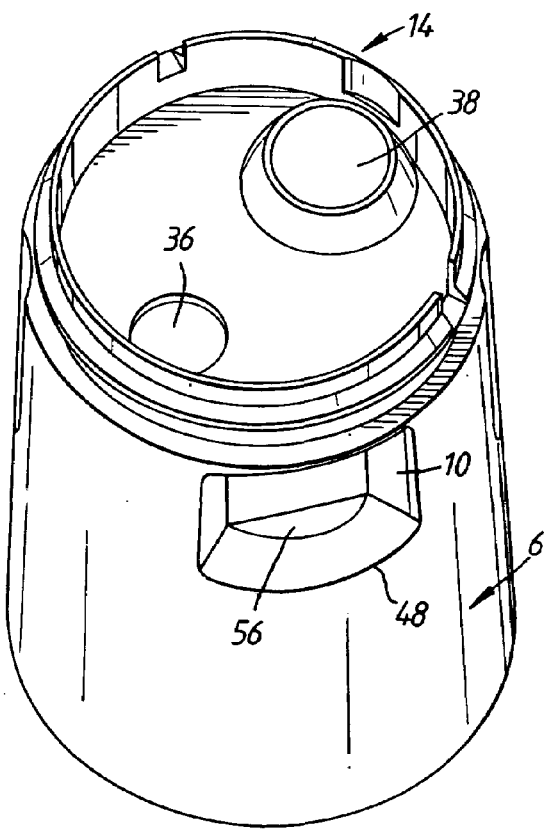
FIGS. 14 and 15 illustrate component parts of a powder inhaler in accordance with a seventh embodiment of the present invention.
Figure 15:
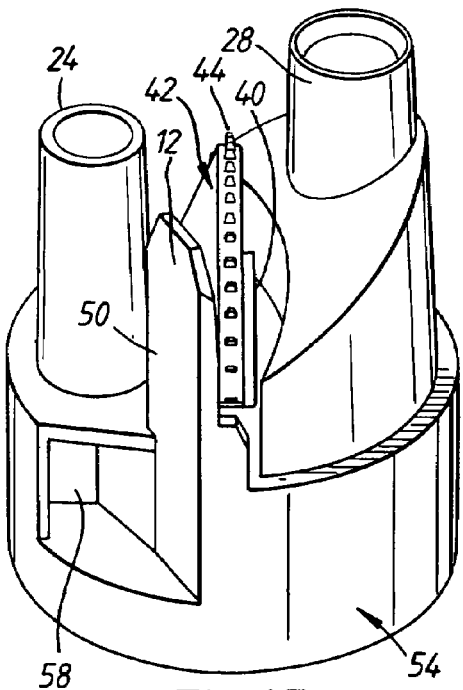

FIGS. 14 and 15 illustrate respectively a body part 52 and a structural unit 54 of a powder inhaler in accordance with a seventh embodiment of the present invention.

This inhaler is a modification of the inhaler of the above-described sixth embodiment. This inhaler differs from the inhaler of the above-described sixth embodiment in that the structural unit 54 includes the supporting means 40 for rotatably supporting the indicating wheel 42 instead of the divider 14 and in that the divider 14 is formed with a substantially flat top surface. In this way, the risk of powder accumulating at this top surface is minimized. This is of particular importance where the top surface of the divider 14 forms the lower wall of the air chamber of the mouthpiece 2.

In each of the inhalers of the above-described fourth to seventh embodiments the storage chamber 28 is crescent-shaped in plan view and thereby provides an increased storage capacity. It will be understood, however, that the storage chamber 28 may be formed as a cylinder as in the above-described known powder inhaler.

Finally, it will be understood by a person skilled in the art that the present invention is not limited to the described embodiments but can be modified in many different ways within the scope of the appended claims.

The invention claimed is:

1. A powder inhaler for administering powder by inhalation, comprising:
   a substantially cylindrical inhaler body having an opening therein;
   an inhalation unit disposed in the inhaler body, the inhalation unit comprising an inhalation channel through which powder is in use inhaled;
   a dosing unit for providing a dose of powder to the inhalation channel disposed in the inhaler body so as to be rotatable about a central axis thereof, wherein the dosing unit comprises a central shaft which is co-axial with the central axis of the inhaler body and has a spiral groove or protrusion on the end face thereof; and
   an indicating wheel for providing an indication as to the usage of the inhaler disposed in the inhaler body, the indicating wheel having a toothed periphery for engaging the spiral groove or protrusion on the shaft and being disposed such that at least a part thereof is visible through the opening and so as to be rotatable within a diametrical plane containing the central axis of the inhaler body, said indicating wheel having first and second side surfaces and being rotatable about an axis that extends through said first and second side surfaces;
   wherein one side surface of the indicating wheel includes at least one indication which is representative of the usage of the inhaler, the inhaler body includes a recess in which the opening is provided, and the opening has a radial component which allows at least a part of the one side surface of the indicating wheel to be viewed.

2. The inhaler according to claim 1, further comprising a storage unit disposed in the inhaler body, the storage unit comprising a storage chamber for storing powder.

3. The inhaler according to claim 2, wherein the storage unit is formed of a transparent material and further comprises a portion which substantially fills the opening.

4. The inhaler according to claim 2, wherein the inhalation unit and the storage unit are formed as a single integral unit.

5. The inhaler according to claim 2, wherein the storage unit further comprises supporting means for rotatably supporting the indicating wheel.

6. The inhaler according to claim 1, further comprising a divider substantially closing one end of the inhaler body.

7. The inhaler according to claim 6, wherein said divider has a major surface, and the recess comprises first and second opposing surfaces which are substantially parallel to the major surface of the divider and at least first and second side surfaces joining the first and second opposing surfaces, the opening being formed in one of the side surfaces.

8. The inhaler according to claim 6, wherein the inhaler body and the divider are formed as a single integral unit.

9. The inhaler according to claim 6, wherein the divider comprises supporting means for rotatably supporting the indicating wheel.

10. The inhaler according to claim 1, wherein the inhaler body further comprises an air inlet in a side wall thereof, the air inlet allowing air to be drawn to the dosing unit and through the inhalation channel.

11. The inhaler according to claim 10, wherein the air inlet is provided in the recess.

12. The inhaler according to claim 1, wherein said first side surface of the indicating wheel includes numerals indicating the number of doses administered or remaining.

13. The inhaler according to claim 1, wherein said first side surface of the indicating wheel includes an at least part circular band of varying width indicating the number of doses administered or remaining.

* * * * *